US00PP27171P3

(12) United States Plant Patent
Tzioros

(10) Patent No.: US PP27,171 P3
(45) Date of Patent: Sep. 20, 2016

(54) ***JASMIUM* PLANT NAMED 'MONHARIKLIA'**

(50) Latin Name: *Jasmium sambac*
Varietal Denomination: MonHariklia

(71) Applicant: Eugenia Tzioros, Matthews, NC (US)

(72) Inventor: Eugenia Tzioros, Matthews, NC (US)

( * ) Notice: Subject to any disclaimer, the term of this patent is extended or adjusted under 35 U.S.C. 154(b) by 79 days.

(21) Appl. No.: 14/121,662

(22) Filed: Oct. 6, 2014

(65) Prior Publication Data

US 2016/0100513 P1 Apr. 7, 2016

(51) Int. Cl.
*A01H 5/02* (2006.01)

(52) U.S. Cl.
USPC ..... Plt./226

(58) Field of Classification Search
USPC ..... Plt./226, 263.1
See application file for complete search history.

*Primary Examiner* — June Hwu
(74) *Attorney, Agent, or Firm* — Cassandra Bright

(57) ABSTRACT

A new and distinct *Jasmium* cultivar named 'MonHariklia' is disclosed, characterized by a long flowering season from April through October, strong, upright plant habit and good branching. Flowers are pure white when mature, and open fully. The new cultivar is a *Jasmium*, suitable for ornamental garden purposes.

2 Drawing Sheets

Latin name of the genus and species: *Jasmium sambac.*
Variety denomination: 'MONHARIKLIA'.

BACKGROUND OF THE INVENTION

The new cultivar is a product of a chance discovery in a backyard setting by the inventor. In June 1997, the inventor, Eugenia Tzioroa discovered an interesting whole plant, naturally occurring mutation. This interesting plant was found by the inventor in Volos, Greece, in a residential garden and transferred to her home in Matthews, N.C.

Plant material of the new variety has not been easily reproduced, with first asexual reproduction occurring in Visalia, Calif. during 2011. In the meanwhile the plants were carefully controlled and held in a confidential location, not accessible to the public. 2 additional generations have been reproduced since 2011, and have shown that the unique features of this cultivar are stable and reproduced true to type.

SUMMARY OF THE INVENTION

The cultivar 'MonHariklia' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonHariklia' These characteristics in combination distinguish 'MonHariklia' as a new and distinct *Jasmium* cultivar:

1. Strong, upright plant habit.
2. Average of 5 main branches per plant, for plants approximately 3 years old.
3. Flowers open fully.
4. Mature flowers are pure white, fading to red-purple.
5. Longer bloom season, typically April through October. Longer with warm weather.
6. Terminal clusters with up to 8 flowers per inflorescence.

COMPARISON TO PARENT VARIETY

The true parent variety is unknown.

COMMERCIAL COMPARISON

'MonHariklia' is best compared to the commercial variety *Jasmium sambac* 'Grand Duke', unpatented. Plants of the new cultivar 'MonHariklia' are similar to plants of 'Grand Duke' in most horticultural characteristics, however, plants of the new cultivar 'MonHariklia' differ in the following:

1. Plants of the new variety have a more upright plant habit. 'Grand Duke' plants are ungainly, nearly vining.
2. Plant growth of the new variety is more controlled, compared to 'Grand Duke'.
3. Flowers of the new variety open fully, whereas flowers of 'Grand Duke' never fully open outwardly.
4. Flowers of the new variety mature to pure White, whereas flowers of 'Grand Duke' remain Green-White.

BRIEF DESCRIPTION OF THE PHOTOGRAPHS

Figure 1:
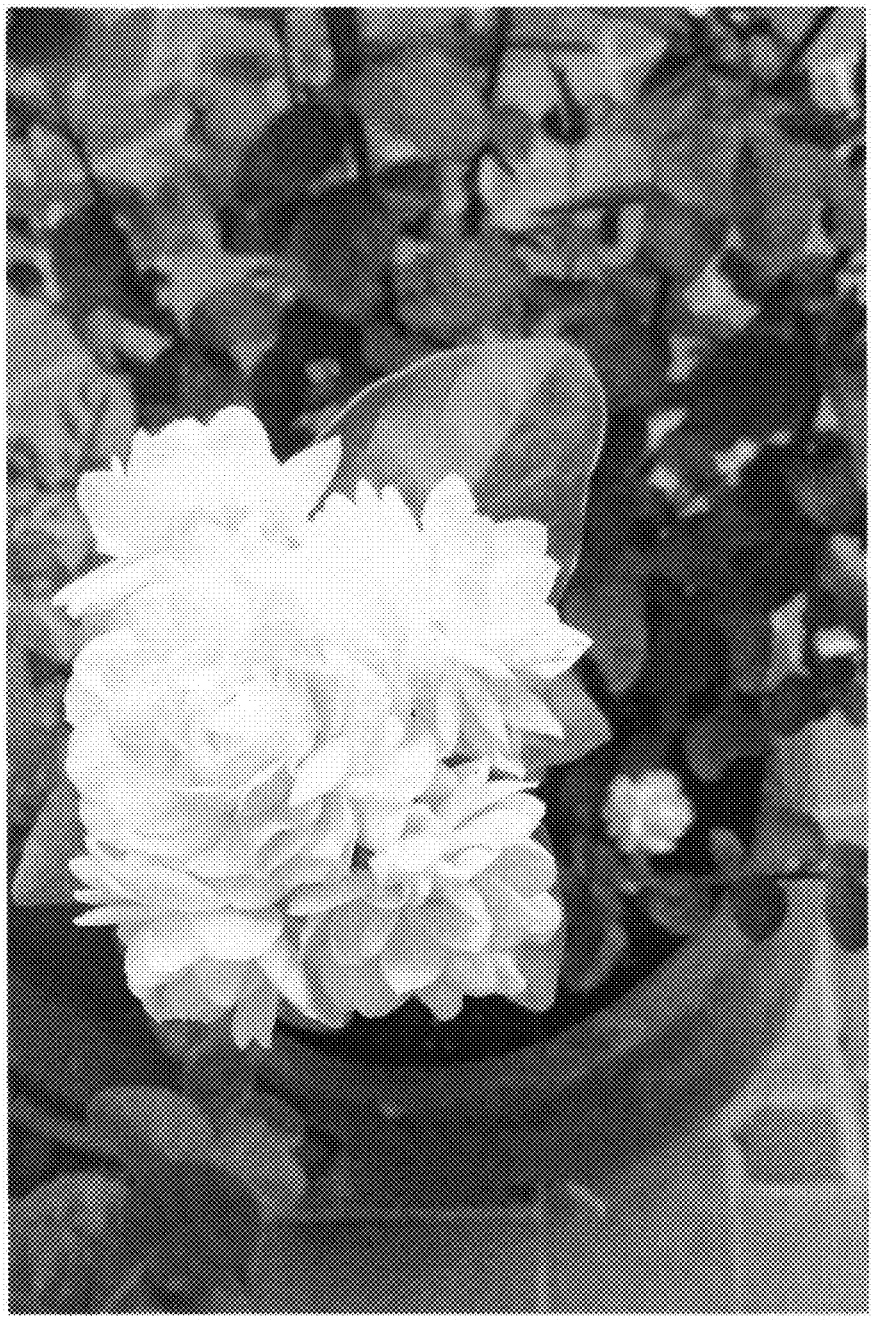

The accompanying photograph in FIG. 1 illustrates in full color a close up of typical foliage and flowers of 'MonHariklia' grown outdoors in Azusa, Calif.

Figure 2:
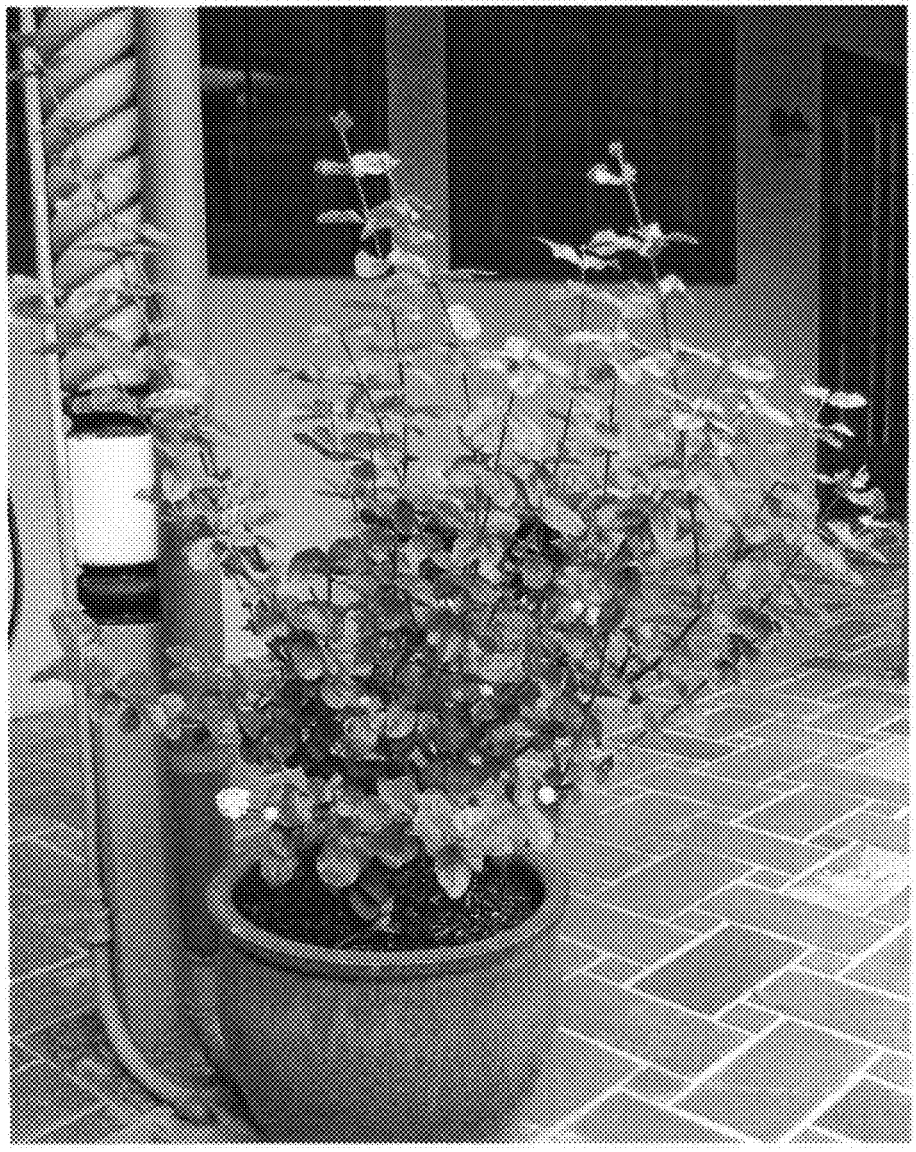

FIG. 2 illustrates in full color a typical plant of 'MonHariklia' grown outdoors in Azusa, Calif. The plant is approximately 3.5 years old, and is planted in an approximately 3 gallon pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonHariklia' plants grown outdoors in Azusa, Calif. Plants are approximately 3.5 years old, in an approximately 3 gallon container. Temperatures ranged from approximately 2° C. to 25° C. at night to 5° C. to 38° C. during the day. Measurements and numerical values represent averages of typical plant types.

Botanical classification: *Jasmium sambac* 'MonHariklia'.

PROPAGATION:

Time to rooting: Approximately 4 to 8 weeks at approximately 20° C. to 30° C. from semi-hardwood cuttings.

Root description: Fine, fibrous young roots. Older roots becoming woody.

PLANT

Growth habit: Upright and outwardly spreading shrub.

Height: Outdoors, after approximately 3.5 years: Approximately 80 cm.

Plant spread: Outdoors, after approximately 3.5 years: Approximately 65 cm.

Branching characteristics: Not free branching, approximately 2 to 3 new branches emerge from a pinch, angled approximately 25 to 45 degrees.

Length of lateral branches: Approximately 10 to 20 cm.

Number of lateral branches: Approximately 5 main lateral branches on a 3.5 year old plant.

Diameter of lateral branches: Approximately 0.5 to 1.2 cm.

Lateral branch strength: Very strong, with some flexibility.

Lateral branch color: Young branches between RHS Yellow-Green 144A and 144B. Mature branches (more than 1 year) near RHS Grey-Brown 199C striated with Greyed-Green 197D.

Texture: Young stems densely and softly pubescent. Mature branches striated, moderately rough.

Number of leaves per lateral branch: Average 24 to 30.

FOLIAGE

Leaf:

*Type*.—Simple.

*Arrangement*.—Opposite, or evenly spaced triad. Rarely, 4 simple leaves emerging from same node.

*Average length*.—Average range 5.0 to 6.5 cm.

*Average width*.—Average range 3.8 to 4.5 cm.

*Shape of blade*.—Ovate.

*Apex*.—Obtuse.

*Base*.—Cordate.

*Attachment*.—Petiolate.

*Margin*.—Entire, very slight undulation to margin.

*Texture of top surface*.—Glabrous.

*Texture of bottom surface*.—Glabrous.

*Appearance of top surface*.—Moderately glossy.

*Appearance of bottom surface*.—Matte.

*Leaf internode length*.—Average range 3.0 to 4.5 cm.

*Color*.—Young foliage upper side: Near RHS Yellow-Green 144A. Young foliage under side: Near RHS Yellow-Green 144A. Mature foliage upper side: Near RHS Green 137A. Mature foliage under side: Near RHS Green 138A.

*Venation*.—Type: Pinnate. Venation color upper side: Main vein near Greyed-Red 182C, laterals near Green 143C. Venation color under side: Near RHS Yellow-Green 144B.

Petiole: Petiole.

*Length*.—Average 0.4 cm.

*Diameter*.—0.2 cm.

*Pubescence*.—Densely and softly pubescent.

*Color*.—Upper Surface Near RHS Green 143A. Lower Surface Near RHS Yellow-Green 144A.

Bloom period:

*Natural season*.—April through October in Southern California.

Inflorescence:

*Arrangement*.—Rotate, double trumpet shaped flowers, with outwardly flared upper petals occur singly, or in clusters 8 on average.

*Diameter*.—Approximately 3.0 cm.

*Depth*.—Approximately 3.9 cm.

Flower:

*Facing direction*.—Out and up.

*Diameter of entire flower*.—Approximately 3.0 cm.

*Depth of flower*.—Approximately 2.0 cm.

*Persistent or self-cleaning*.—Self-cleaning corolla, calyx typically persists.

*Fragrance*.—Very strong, sweet jasmine scent occurs consistently throughout all hours.

Petals:

*Quantity*.—2 individual corolla tubes present, one inside of the other, forming a full double flower. Each corolla tube with approximately 25 unfused petal segments each, emerging from the tube opening.

*Corolla tube*.—Tube Length: Approximately 1.0 cm. Tube Opening Width: Approximately 0.7 cm. Tube Base Width: Approximately 0.4 cm.

*Color*.—Inner surface at first opening: Near RHS Green-White 157D. Outer surface at first opening: Near RHS Yellow-Green 145C. Inner surface at maturity: Near RHS White 155A. Outer surface at maturity: Near RHS White 155A. Inner surface at fading: Near RHS White 155A, moderately streaked with Red-Purple 59B. Tube opening is entirely Red-Purple 59A. Red-Purple streaking increases with flower age. Outer surface at fading: Near RHS Red-Purple 59B and 59A, occurring in stripes.

*Unfused petal segments*.—Length: Approximately 1.0 cm. Width: Approximately 1.0 cm. Apex: Obtuse, or mucronate, both apices occurring within one flower. Shape: Ovate. Margin: Entire. Arrangement: Rotate, overlapping. Texture: Glabrous upper and lower surfaces. Appearance: Moderately shiny upper surface, matte lower surface.

*Color*.—Upper surface at first opening: Near RHS Green-White 157D. Lower surface at first opening: Near RHS Green-White 157C. Upper surface at maturity: Near RHS White 155A. Lower surface at maturity: Near RHS White 155A. Upper surface at fading: Near RHS White 155A, lightly to moderately flushed with Red-Purple 59B. Flushing increases with flower age. Lower surface at fading: Near RHS White 155A, heavily flushed with Red-Purple 59B and 59A.

*Calyx/sepals*.—Arrangement/Shape: Funnel shaped, upper ⅓rd unfused. Sepals per flower: Average 10 fused into funnel shape ⅔rds from base. Unfused Shape: Narrow deltoid. Length: Entire calyx length approximately 1.5 cm, unfused section approximately 0.5 cm. Width: Entire calyx width approximately 0.5 cm, unfused section approximately 0.25 cm. Apex: Acute. Base: Fused. Margin: Entire. Texture: Minute pubescence outer surface, inner surface glabrous. Color: Upper Surface: RHS Yellow-Green 145A. Lower Surface: RHS Yellow-Green 145A.

*Peduncle*.—Length: About 2.5 cm. Diameter: About 0.2 cm. Color: RHS Green 137B. Texture: Densely and softly pubescent. Orientation: Straight, occurring at no angle, arising directly from branch. Other: Calyx like structure occurs at the upper portion of the peduncle. Similar to the corolla within a corolla structure of the petal arrangement, a second calyx like structure occurs at the base of the ovary. For description purposes, this will be described as the "Secondary Calyx".

*Secondary calyx*.—Arrangement/Shape: Funnel shaped, upper ½$^{th}$ unfused. Sepals per flower: Average 5 fused into funnel shape 50% from base. Unfused Shape: Narrow deltoid. Length: Entire calyx length approximately 1.0 cm, unfused section approximately 0.5 cm. Width: Entire calyx width approximately 0.5 cm, unfused section approximately 0.15 cm. Apex: Acute. Base: Fused. Margin: Entire, Texture: Minute pubescence outer surface, inner surface glabrous. Color: Upper Surface: RHS Yellow-Green 145A. Lower Surface: RHS Yellow-Green 145A.

*Pedicel*.—Length: Average approximately 0.8 cm. Diameter: About 0.15 cm. Texture: Densely and softly pubescent. Color: RHS Green 137B. Orientation: Straight.

*Stamens*.—Number: 5. Filament length: About 0.4 cm. Filament color: Near RHS Yellow-Green 145C.

*Anthers*.—Length: About 0.1 cm. Shape: Linear. Color: RHS Greyed-Red 181B. Pollen: Pollen production not observed.

*Pistil*.—Number: 1. Length: About 1.4 cm. Style: Length: About 0.7 cm. Color: RHS Yellow-Green 145C. Stigma: Shape: linear. Color: RHS Green 144 D. Ovary Color: RHS Green 144 C.

OTHER CHARACTERISTICS:

Disease and pest resistance: Not observed to be susceptible nor resistant to normal diseases and pests of *Jasmium sambac*.

Drought tolerance: No drought tolerance.

Temperature tolerance: Suitable for USDA zones 10 and 11.

Fruit/seed production: Not observed to date.

What is claimed is:

1. A new and distinct cultivar of *Jasmium* plant named 'MonHariklia' as herein illustrated and described.

* * * * *